United States Patent
Perschbacher et al.

(10) Patent No.: US 11,357,441 B2
(45) Date of Patent: Jun. 14, 2022

(54) SYSTEMS AND METHODS FOR DETECTING AND REPORTING ARRHYTHMIAS

(71) Applicant: Cardiac Pacemakers, Inc., St. Paul, MN (US)

(72) Inventors: David L. Perschbacher, Coon Rapids, MN (US); Sunipa Saha, Shoreview, MN (US); Deepa Mahajan, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 582 days.

(21) Appl. No.: 16/260,817

(22) Filed: Jan. 29, 2019

(65) Prior Publication Data
US 2019/0231207 A1    Aug. 1, 2019

Related U.S. Application Data

(60) Provisional application No. 62/625,239, filed on Feb. 1, 2018.

(51) Int. Cl.
*A61N 1/37* (2006.01)
*A61B 5/361* (2021.01)
(Continued)

(52) U.S. Cl.
CPC ............ *A61B 5/361* (2021.01); *A61B 5/0006* (2013.01); *A61B 5/0031* (2013.01); *A61B 5/363* (2021.01);
(Continued)

(58) Field of Classification Search
CPC ....... A61B 5/361; A61B 5/363; A61B 5/0031; A61B 5/0006; A61B 5/7282; A61B 5/283;
(Continued)

(56) References Cited

U.S. PATENT DOCUMENTS

| | | | |
|---|---|---|---|
| 2007/0038253 A1* | 2/2007 | Kim | A61N 1/3622 607/4 |
| 2011/0112597 A1* | 5/2011 | Snell | A61N 1/37235 607/27 |

(Continued)

FOREIGN PATENT DOCUMENTS

| | | |
|---|---|---|
| CN | 111670003 A | 9/2020 |
| WO | WO-2019152376 A1 | 8/2019 |

OTHER PUBLICATIONS

"European Application Serial No. 19707920.5, Response filed Mar. 11, 2021 to Communication pursuant to Rules 161(1) and 162 EPC dated Sep. 9, 2020", 3 pgs.

(Continued)

*Primary Examiner* — Eugene T Wu
(74) *Attorney, Agent, or Firm* — Schwegman Lundberg & Woessner, P.A.

(57) ABSTRACT

Systems and methods for managing cardiac arrhythmias are discussed. A data management system receives a first detection algorithm including a detection criterion for detecting a cardiac arrhythmia. An arrhythmia detector detects arrhythmia episodes from a physiologic signal using a second detection algorithm that is different from and has a higher sensitivity for detecting the cardiac arrhythmia than the first detection algorithm. The arrhythmia detector assigns a detection indicator to each of the detected arrhythmia episodes. The detection indicator indicates a likelihood that the detected arrhythmia episode satisfies the detection criterion of the first detection algorithm. The system prioritizes the detected arrhythmia episodes according to the assigned detection indicators, and outputs the arrhythmia episodes to a user or a process according to the episode prioritization.

20 Claims, 6 Drawing Sheets

(51) Int. Cl.
| | |
|---|---|
| *A61N 1/05* | (2006.01) |
| *A61B 5/00* | (2006.01) |
| *G16H 40/63* | (2018.01) |
| *G16H 15/00* | (2018.01) |
| *G16H 50/30* | (2018.01) |
| *A61B 5/363* | (2021.01) |
| *A61N 1/39* | (2006.01) |
| *A61N 1/08* | (2006.01) |
| *A61N 1/365* | (2006.01) |
| *A61B 5/0205* | (2006.01) |
| *A61B 5/024* | (2006.01) |
| *A61B 5/145* | (2006.01) |
| *A61B 5/11* | (2006.01) |
| *A61N 1/362* | (2006.01) |
| *A61B 5/0215* | (2006.01) |
| *A61B 5/0245* | (2006.01) |
| *A61B 5/08* | (2006.01) |
| *A61B 5/283* | (2021.01) |
| *A61B 5/316* | (2021.01) |

(52) U.S. Cl.
CPC .......... *A61B 5/7282* (2013.01); *A61N 1/0504* (2013.01); *G16H 15/00* (2018.01); *G16H 40/63* (2018.01); *G16H 50/30* (2018.01); *A61B 5/0205* (2013.01); *A61B 5/0215* (2013.01); *A61B 5/0245* (2013.01); *A61B 5/02405* (2013.01); *A61B 5/02438* (2013.01); *A61B 5/0816* (2013.01); *A61B 5/1118* (2013.01); *A61B 5/14542* (2013.01); *A61B 5/283* (2021.01); *A61B 5/316* (2021.01); *A61B 5/6823* (2013.01); *A61B 5/7264* (2013.01); *A61B 5/7275* (2013.01); *A61N 1/08* (2013.01); *A61N 1/365* (2013.01); *A61N 1/3624* (2013.01); *A61N 1/3655* (2013.01); *A61N 1/36521* (2013.01); *A61N 1/36535* (2013.01); *A61N 1/36564* (2013.01); *A61N 1/36578* (2013.01); *A61N 1/37* (2013.01); *A61N 1/3704* (2013.01); *A61N 1/395* (2013.01); *A61N 1/3956* (2013.01); *A61N 1/3987* (2013.01); *A61N 1/39622* (2017.08)

(58) Field of Classification Search
CPC ... A61B 5/316; A61B 5/0205; A61B 5/02438; A61B 5/14542; A61B 5/1118; A61B 5/0215; A61B 5/7275; A61B 5/7264; A61B 5/0245; A61B 5/02405; A61B 5/0816; A61B 5/6823; G16H 40/63; G16H 15/00; G16H 50/30; A61N 1/0504; A61N 1/3655; A61N 1/36535; A61N 1/36564; A61N 1/3624; A61N 1/3987; A61N 1/36578; A61N 1/365; A61N 1/395; A61N 1/36521; A61N 1/3704; A61N 1/39622; A61N 1/3956; A61N 1/37; A61N 1/08
See application file for complete search history.

(56) References Cited

U.S. PATENT DOCUMENTS

2015/0080674 A1* 3/2015 Drew ................ A61N 1/37252
600/301
2017/0290550 A1* 10/2017 Perschbacher ....... A61B 5/7221

OTHER PUBLICATIONS

"International Application Serial No. PCT/US2019/015584, International Preliminary Report on Patentability dated Aug. 13, 2020", 7 pgs.
"International Application Serial No. PCT/US2019/015584, International Search Report dated Apr. 17, 2019", 4 pgs.
"International Application Serial No. PCT/US2019/015584, Written Opinion dated Apr. 17, 2019", 5 pgs.

* cited by examiner

SYSTEMS AND METHODS FOR DETECTING AND REPORTING ARRHYTHMIAS

CLAIM OF PRIORITY

This application claims the benefit of priority under 35 U.S.C. § 119(e) of U.S. Provisional Patent Application Ser. No. 62/625,239, filed on Feb. 1, 2018, which is herein incorporated by reference in its entirety.

TECHNICAL FIELD

This document relates generally to medical devices, and more particularly, to systems, devices and methods for detecting and reporting arrhythmias.

BACKGROUND

Implantable medical devices (IMDs) have been used for monitoring patient health condition or disease states and delivering therapies. For example, implantable cardioverter-defibrillators (ICDs) are used to monitor certain abnormal heart rhythms. Some IMDs may be used to monitor progression of a chronic disease, such as worsening of cardiac performance due to congestive heart failure (CHF). In addition to diagnostic capabilities, the IMDs may also provide therapies to treat or alleviate certain medical conditions, such as cardiac electrostimulation therapies to treat cardiac arrhythmias or to rectify cardiac dyssynchrony in CHF patients.

The IMDs may record medical data associated with detected medical events such as a cardiac arrhythmia or worsening heart failure (WHF). The IMDs may be interconnected to a patient management system via a data communication network. Device data, such as the medical data associated with the detected medical events, may be transmitted to a patient management system, through which a healthcare professional may remotely follow up with the patients or assess functions of the IMDs on a regular basis.

OVERVIEW

A patient management system may manage a large volume of alert notifications corresponding to medical events detected from ambulatory medical devices (AMDs). For example, in managing AMD patients in a clinic, the patient management system may frequently receive alert notifications on various medical events, such as cardiac arrhythmia episodes or worsening heart failure (WHF) events detected by the AMDs. The AMDs detect medical events (e.g., cardiac arrhythmias) using detection parameters programmed by a user (e.g., a clinician), generate medical event episodes that may be later reviewed by a clinician to adjudicate the device-detected medical events, perform offline data analysis, schedule patient follow-up visits, or reprogram the AMDs, among others.

To conserve device memory, conventional AMDs generally generate event episodes only if a target medical event is detected (i.e., a positive detection). Physiologic data acquired during, or optionally before or after, a detected medical event may be stored for that event episode. No episode is generally generated if a target medical event is not detected (i.e., a negative detection). For example, an arrhythmia management device generates an arrhythmia episode if it detects a specified type of arrhythmia (e.g., an atrial fibrillation, or ventricular tachycardia), but no or little physiologic information is recorded if no target arrhythmia is detected. Stored episodes for positive detections may provide useful diagnostic information. For example, an offline review or analysis of these device stored episodes may reveal false positive (FP) detections made by the AMD. A clinician may then reprogram the AMD accordingly to reduce future FP detections and improve arrhythmia detection specificity. Just like the device-generated positive detections may sometimes include FP detections, device-generated negative detections made sometimes include false negative (FN) detections. However, with no episode or very limited physiologic data recorded for these negative event detections, recognizing FN detections can be technically more difficult, if not impossible, than recognition of the FP detections.

Some FN detections can be attributed to inappropriate programming of an arrhythmia detector. For example, a very high detection threshold may result in a low sensitivity to a medical event of interest. A negative detection of an arrhythmia event that fails to satisfy the arrhythmia detection threshold by a small margin may nevertheless be a FN detection. The FN detections may reduce the detection sensitivity, missing some medical events that need to be treated or otherwise require medical attention. Therefore, although event episode management in current AMDs may facilitate recognition of FP detections, there remains an unmet need for storing and making available medical data to facilitate offline analysis and recognition of FN detections, and thereby improving detection sensitivity in an AMD.

This document discusses, among other things, systems, devices, and methods for detecting and managing cardiac arrhythmias. A data management system may receive a user input of a first algorithm including a detection criterion for detecting a cardiac arrhythmia. The system includes an arrhythmia detector circuit that determines a second detection algorithm different from and has a higher sensitivity than the cardiac arrhythmia than the first detection algorithm, and detects an arrhythmia from a physiologic signal using the second detection algorithm. The arrhythmia detector circuit may assign a detection indicator to the detected arrhythmia episode. The detection indicator indicates a likelihood that the detected arrhythmia episode would satisfy the detection criterion of the first detection algorithm. A control circuit may prioritize the detected arrhythmia episode according to the assigned detection indicators. The arrhythmia episodes may be output to a user or a process according to the episode prioritization.

Example 1 is a system for monitoring cardiac arrhythmia. The system comprises an arrhythmia detector circuit and an event prioritizer circuit. The arrhythmia detector circuit is configured to receive a physiologic signal and a first detection algorithm having a first sensitivity, the first detection algorithm including a detection criterion for detecting a cardiac arrhythmia. The arrhythmia circuit is configured to detect an arrhythmia episode from the physiologic signal using a second detection algorithm having a second sensitivity higher than the first sensitivity of the first detection algorithm for detecting the cardiac arrhythmia, than the first detection algorithm, and assign a detection indicator to the detected arrhythmia episode. The detection indicator indicates a likelihood that the detected arrhythmia episode satisfies the detection criterion of the first detection algorithm. The event prioritizer circuit is configured to prioritize the detected arrhythmia episode according to the assigned detection indicators.

In Example 2, the subject matter of Example 1 optionally includes the arrhythmia detector circuit that may be configured to generate the second detection algorithm by adjusting one or more detection parameters of the first detection algorithm.

In Example 3, the subject matter of Example 2 optionally includes the one or more detection parameters including a first detection threshold, and the arrhythmia detector circuit may be configured to generate the second detection algorithm by reducing the first detection threshold to a lower second detection threshold.

In Example 4, the subject matter of any one or more of Examples 1-3 optionally includes a memory circuit configured to store the detected arrhythmia episode, and a control circuit configured to prioritize storage of the detected arrhythmia episode in the memory circuit according to the prioritization of the arrhythmia episode.

In Example 5, the subject matter of Example 4 optionally includes the control circuit that may be configured to prioritize storage of a detected arrhythmia episode that satisfies the detection criterion of the first detection algorithm over storage of another detected arrhythmia episode that does not satisfy the detection criterion of the first detection algorithm.

In Example 6, the subject matter of any one or more of Examples 1-5 optionally includes an ambulatory device communicatively coupled to an external device. The ambulatory device may include a transceiver circuit and one or more of the arrhythmia detector circuit and the event prioritizer circuit. The transceiver circuit may be configured to transmit the detected arrhythmia episode to the external device according to the prioritization of the arrhythmia episode.

In Example 7, the subject matter of Example 6 optionally includes a control circuit configured to prioritize transmission of a detected arrhythmia episode that satisfies the detection criterion of the first detection algorithm over transmission of another detected arrhythmia episode that does not satisfy the detection criterion of the first detection algorithm.

In Example 8, the subject matter of any one or more of Examples 1-7 optionally includes an output circuit that may be configured to present the detected arrhythmia episode to a user or a process, and a control circuit configured to prioritize presentation of the detected arrhythmia episode according to the prioritization of the arrhythmia episode.

In Example 9, the subject matter of Example 8 optionally includes the control circuit that may be configured to prioritize a presentation of a detected arrhythmia episode that satisfies the detection criterion of the first detection algorithm over a presentation of another arrhythmia episode that does not satisfy the detection criterion of the first detection algorithm.

In Example 10, the subject matter of Example 9 optionally includes a user interface configured to generate an alert of a detection of one or more arrhythmia episodes that do not satisfy the detection criterion of the first detection algorithm, and to display, in response to a user command, the detected arrhythmia episode that do not satisfy the detection criterion of the first detection algorithm.

In Example 11, the subject matter of Example 10 optionally includes the user interface that may further be configured to display a detected arrhythmia episode that satisfies the detection criterion of the first detection algorithm, and in response to a user command, display the detected arrhythmia episode that do not satisfy the detection criterion of the first detection algorithm.

In Example 12, the subject matter of any one or more of Examples 1-11 optionally includes the event prioritizer circuit that may be configured to prioritize the detected arrhythmia episode further using a comparison to a patient-triggered episode.

In Example 13, the subject matter of any one or more of Examples 1-12 optionally includes the event prioritizer circuit that may be configured to prioritize the detected arrhythmia episode further using a comparison to patient symptom.

In Example 14, the subject matter of any one or more of Examples 1-13 optionally includes the output circuit that may be configured to generate a recommendation for adjusting one or more parameters associated with the first detection algorithm.

In Example 15, the subject matter of any one or more of Examples 1-14 optionally includes a therapy circuit configured to generate a therapy for treating arrhythmia in response to the detection of the arrhythmia episode.

Example 16 is a method for monitoring cardiac arrhythmias using a cardiac monitoring system. The method comprises steps of: receiving a user programming of a first detection algorithm having a first sensitivity, the first detection algorithm including a detection criterion for detecting a cardiac arrhythmia; determining a second detection algorithm based on the received first detection algorithm via an arrhythmia detector circuit, the second detection algorithm having a second sensitivity higher than the first sensitivity of the first detection algorithm; assigning a detection indicator to the detected arrhythmia episode via the arrhythmia detector circuit, the detection indicator indicating a likelihood that the detected arrhythmia episode satisfies the detection criterion of the first detection algorithm; and prioritizing the detected arrhythmia episode via an event prioritizer circuit according to the assigned detection indicators.

In Example 17, the subject matter of Example 16 optionally includes, wherein determining the second detection algorithm includes adjusting one or more detection parameters of the first detection algorithm.

In Example 18, the subject matter of Example 17 optionally includes adjusting the one or more detection parameters includes reducing a first detection threshold of the first detection algorithm to a lower second detection threshold of the second detection algorithm.

In Example 19, the subject matter of any one or more of Examples 16-18 optionally includes storing the detected arrhythmia episode in a memory circuit according to the prioritization of the arrhythmia episode.

In Example 20, the subject matter of any one or more of Examples 16-19 optionally includes transmitting the detected arrhythmia episode to an external device according to the prioritization of the arrhythmia episode.

In Example 21, the subject matter of any one or more of Examples 16-20 optionally includes displaying a detected arrhythmia episode that satisfies the detection criterion of the first detection algorithm, and in response to a user command, displaying the detected arrhythmia episode that do not satisfy the detection criterion of the first detection algorithm.

Example 22 is a system for monitoring cardiac arrhythmia. The system comprises an arrhythmia detector circuit configured to receive a physiologic signal, determine a presence of an arrhythmia in the physiologic signal using a first detection algorithm having a first sensitivity, and for the same physiologic signal, determine the presence of the arrhythmia in the physiologic signal using a second detection algorithm having a second sensitivity higher than the first sensitivity.

Cardiac arrhythmia detection as discussed in this document may improve functionality of a medical device such as an AMD. As previously discussed, conventional medical system or device do not record episode data for negative detections as it does for positive detections, thus making offline data review and analysis and FN detection recognition technologically challenging tasks. This document discusses a technological solution to this problem by using an automatically generated detection algorithm that has a higher sensitivity in detecting the target arrhythmia event than a user-specified algorithm. The more sensitive detection algorithm allows the system to detect additional arrhythmia events that would otherwise be missed by the less sensitive user-specified algorithm, and store additional episodes (which are referred to as secondary episodes in this document) for these arrhythmia events. Respective detection indicators may be used to distinguish the secondary episodes from those arrhythmia events that would also be detected by the user-specified algorithm (which are referred as primary episodes in this document). A user (e.g., a clinician) may selectively inspect and adjudicate the secondary episodes, and adjust arrhythmia detection in an AMD based on the adjudication (e.g., recognition of FN episodes). For example, if an AMD does not detect the target medical event (e.g., arrhythmia) under a user-specified device setting, but the patient has experienced symptoms of arrhythmia, a clinician may choose to retrieve and review secondary episodes to ascertain proper device programming. Based on the adjudication of the secondary episodes, a user may program the AMD with an individualized sensitivity level (e.g., detection threshold) for the arrhythmia detector. This may in turn reduce future FN detections and improve arrhythmia detection sensitivity; while at the same time substantially maintains arrhythmia detection specificity, thereby improving the overall functionality of the AMD.

The subject matter discussed herein requires little to no additional cost or system complexity on top of a conventional medical event detector system. The secondary episodes maybe generated and managed using the same episode management unit as used for generating, storing, and presenting the primary episodes. The prioritized episode storage, reporting, and transmission as discussed in this document improves efficiency of system resources usage (e.g., device memory and communication bandwidth usage). With improved arrhythmia detection performance, arrhythmia events may be timely and accurately detected, while fewer unnecessary drugs and procedures may be scheduled, prescribed, or provided, and an overall system cost savings may be realized.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting and managing cardiac arrhythmias. In an embodiment, a data management system receives a user programming of a first detection algorithm including a detection criterion for detecting a cardiac arrhythmia. An arrhythmia detector detects an arrhythmia episode from a physiologic signal using an automatically generated second detection algorithm different from, and has a higher sensitivity than the cardiac arrhythmia than, the first detection algorithm. The arrhythmia detector circuit may assign a detection indicator to the detected arrhythmia episode. The detection indicator indicates a likelihood that the detected arrhythmia episode satisfies the detection criterion of the first detection algorithm. The system may prioritize the detected arrhythmia episode according to the assigned detection indicator, and output the arrhythmia episode to a user or a process according to the episode prioritization. Although the present document is focused on monitoring arrhythmia, this is meant to mean only by way of example and not limitation. The systems and methods discussed here may be modified to monitor other medical events, such as a worsening heart failure event.

Figure 1:
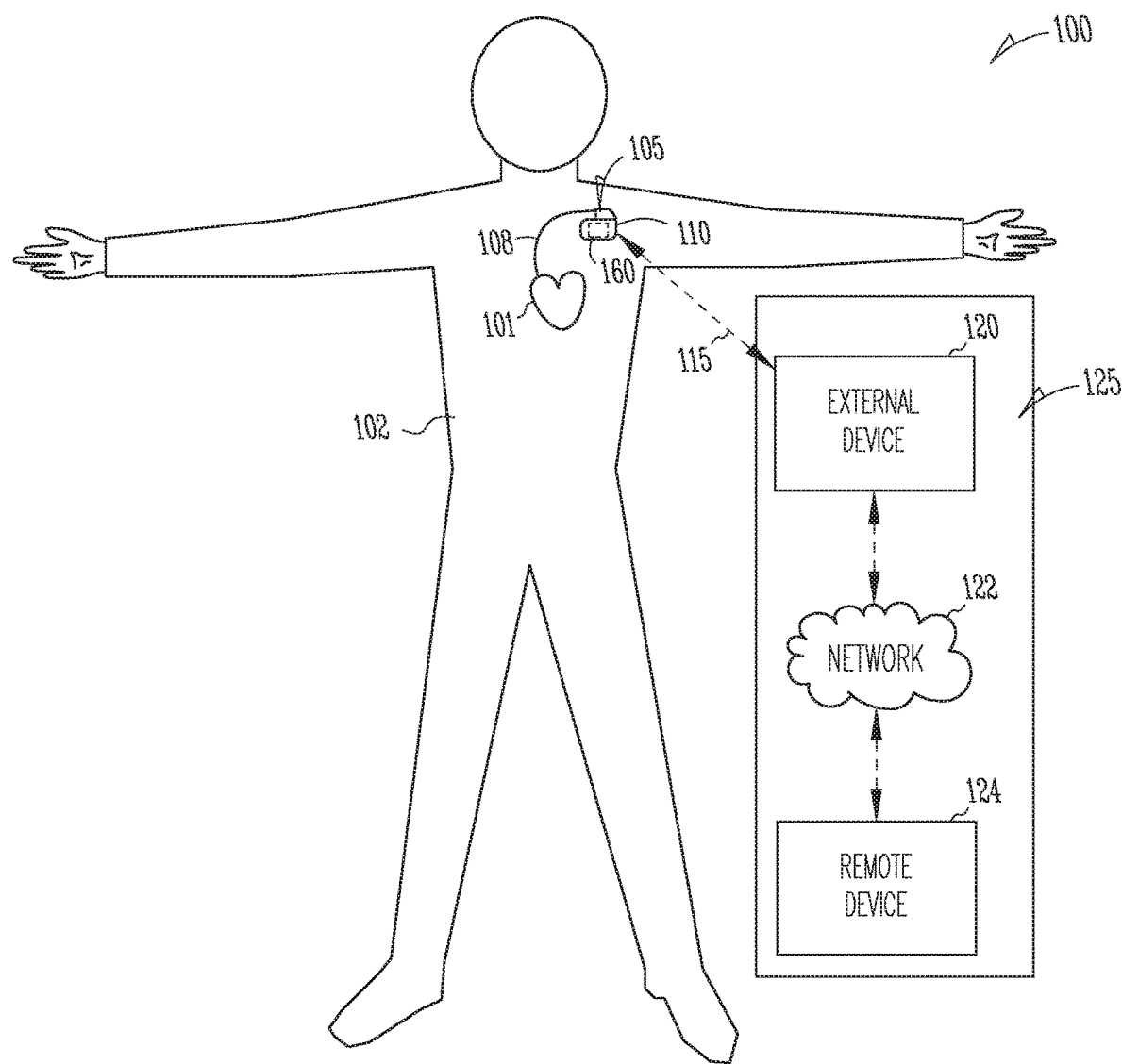
FIG. 1 illustrates generally an example of a patient management system and portions of an environment in which the system may operate.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125. The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiologic signal, such as by using a physiologic sensor or the electrodes associated with the lead system 108. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

In an example, the AMD 110 may include a medical event detector circuit 160 for detecting a specified type of medical event. The physiologic event may include a cardiac arrhythmia such as atrial fibrillation, atrial flutter, atrial tachycardia, supraventricular tachycardia, ventricular tachycardia, or ventricular fibrillation, among other atrial or ventricular brady- or tachy-arrhythmia. In another example, the physiologic event may include a chronic medical condition, such as worsening heart failure (WHF) event. For a user-specified detection algorithm (or a user-specified value of a detection parameter such as a detection threshold), the medical event detector circuit 160 may detect the specified medical event using an algorithm different from, and more sensitive than the user-specified detection algorithm. The medical event detector circuit 160 may assign to the detected physiologic event a priority indicator indicating a likelihood that the detected event episode satisfies the detection criterion of the user-specified detection algorithm. Event episodes, including physiologic data collected during the detected medical events, may be stored in the AMD 110, or be output to a user or a process such as transmitted to an external device, according to the event prioritization.

The AMD 110 may optionally include a therapy circuit to generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmias, such as syncope, congestive heart failure, or stroke, among others. Examples of the anti-arrhythmic therapy may include cardiac pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmias or complications from arrhythmias.

The external system 125 may include a dedicated hardware/software system such as a programmer, a remote server-based patient management system, or alternatively a system defined predominantly by software running on a standard personal computer. The external system 125 may manage the patient 102 through the AMID 110 connected to the external system 125 via a communication link 115. This may include, for example, programming the AMD 110 to perform one or more of acquiring medical data, performing at least one self-diagnostic test (such as for a device operational status), analyzing the medical data to detect a cardiac arrhythmias, or optionally delivering or adjusting a therapy to the patient 102. Additionally, the external system 125 may receive device data from the AMD 110 via the communication link 115. Examples of the device data received by the external system 125 may include real-time or stored medical data from the patient 102, diagnostic data such as detection of cardiac arrhythmias or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data may be collected by the AMD 110, among other data acquisition sensors or devices associated with the patient 102. The server may include a memory device to store the patient data in a patient database. The server may include an alert analyzer circuit to evaluate the collected patient data to determine if specific alert condition is satisfied. Satisfaction of the alert condition may trigger a generation of alert notifications. Alternatively or additionally, the alert conditions may be evaluated by the AMD 110. By way of example, alert notifications may include a Web page update, phone or pager call, E-mail, SMS, text or "Instant" message, as well as a message to the patient and a simultaneous direct notification to emergency services and to the clinician. Other alert notifications are possible.

The remote device 124 may additionally include one or more locally configured clients or remote clients securely connected over the network 122 to the server. Examples of the clients may include personal desktops, notebook computers, mobile devices, or other computing devices. Users, such as clinicians or other qualified medical specialists, may use the clients to securely access stored patient data assembled in the database in the server, and to select and prioritize patients and alerts for health care provisioning. In addition to generating alert notifications, the remote device 124, including the server and the interconnected clients, may also execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a user such as the patient or a clinician, or to a process including, for example, an instance of a computer program executable in a microprocessor. In an example, the process may include an automated generation of recommendations for anti-arrhythmic therapy, or a recommendation for further diagnostic test or treatment. In an example, the external device 120 or the remote device 124 may include a respective display unit for displaying the physiologic or functional signals, or alerts, alarms, emergency calls, or other forms of warnings to signal the detection of arrhythmias. In some examples, the external system 125 may include an external data processor configured to analyze the physiologic or functional signals received by the AMD 110, and to confirm or reject the detection of arrhythmias. Computationally intensive algorithms, such as machine-learning algorithms, may be implemented in the external data processor to process the data retrospectively to detect cardiac arrhythmias.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
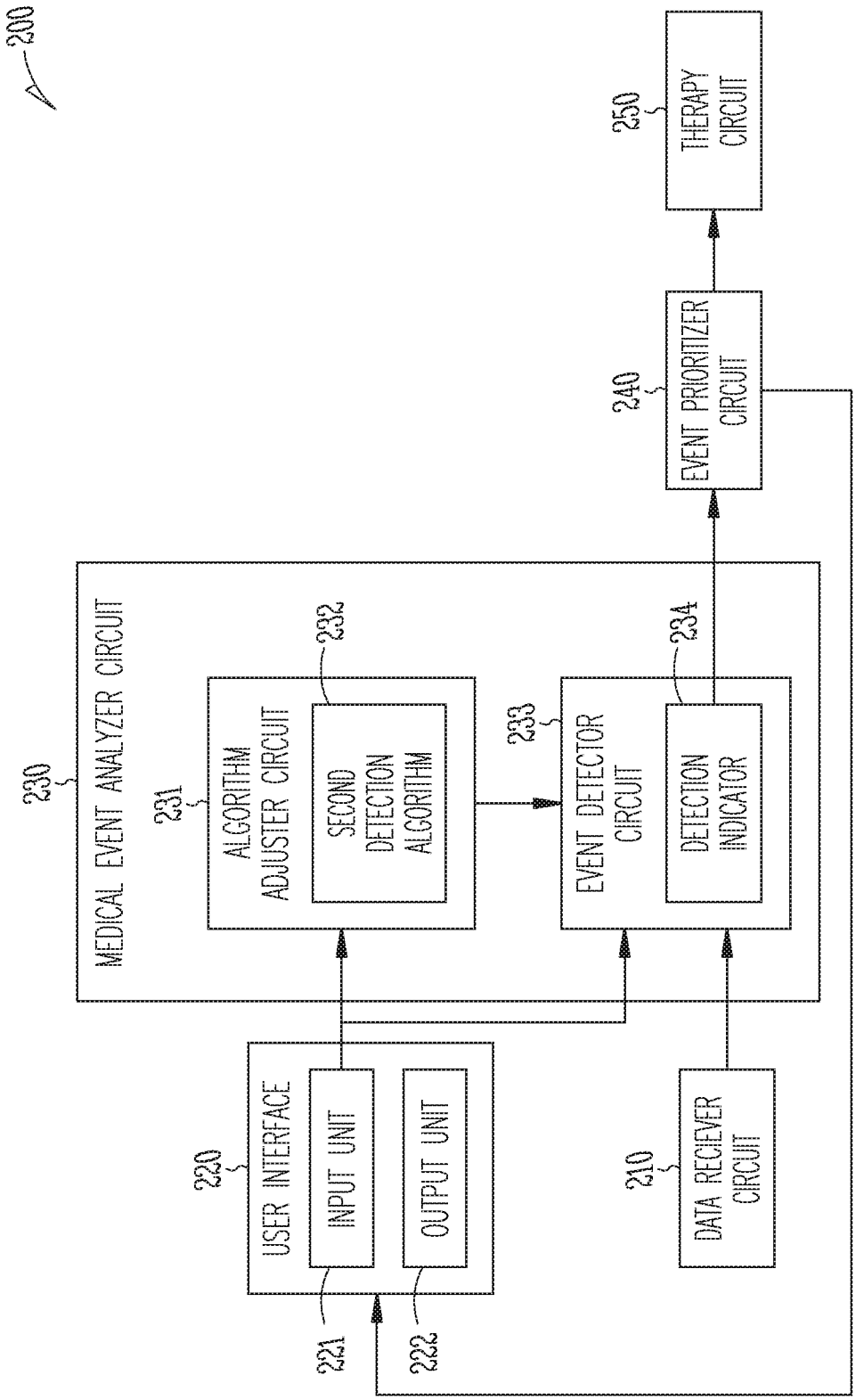
FIG. 2 illustrates generally an example of a medical event detection system for monitoring target medical event, such as a cardiac arrhythmia.

FIG. 2 illustrates generally an example of a medical event detection system 200 for monitoring target medical event, such as a cardiac arrhythmia. At least a portion of the medical event detection system 200 may be implemented in the AMD 110, the external system 125 such as one or more of the external device 120 or the remote device 124, or distributed between the AMD 110 and the external system 125. As illustrated in FIG. 2, the medical event detection system 200 may include one or more of a data receiver circuit 210, a user interface 220, a medical event analyzer circuit 230, an event prioritizer circuit 240, and an optional therapy circuit 250.

The data receiver circuit 210 may receive physiologic data acquired from a patient. In an example, the data receiver circuit 210 may include a sensing circuit including sense amplifiers coupled to one or more implantable, wearable, or otherwise ambulatory sensors or electrodes associated with the patient to sense one or more physiologic signals from a patient. The sensors may be incorporated into, or otherwise associated with an ambulatory device such as the AMD 110. In some examples, the data receiver circuit 210 may receive the physiologic signals from a storage device, such as an electronic medical record (EMR) system. Examples of the physiologic signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The data receiver circuit 210 may include one or more sub-circuits to digitize, filter, or perform other signal conditioning operations on the received physiologic signal.

The user interface 220 may include an input unit 221 and an output unit 222. In an example, at least a portion of the user interface 220 may be implemented in the external system 125. The input unit 221 may receive user input for programming the medical event analyzer circuit 230 and the event prioritizer circuit 240, such as parameters for detecting a target medical event, or for prioritizing episodes of the detected events. The input unit 221 may include an input device such as a keyboard, on-screen keyboard, mouse, trackball, touchpad, touch-screen, or other pointing or navigating devices. In some examples, via the user interface 220, a user may interactively annotate or mark on the presentation of the detected medical event, such as by adjudicating the received episode.

The user interface 220 may receive a user programming of a first detection algorithm via the input unit 221 for detecting a target medical event, such as target cardiac arrhythmia. The first detection algorithm may define a detection criterion that a signal metric (X) must satisfy to make a positive detection of the target medical event. The signal metric X may be generated from a physiologic signal. Alternatively, the signal metric X is a composite metric generated using two or more physiologic signals. In an example, the detection criterion includes a threshold value ($X_{TH}$) for the signal metric or composite metric X, and the first detection algorithm is associated with a first threshold value $X_{TH-1}$. A positive detection of the target medical event may be made if X exceeds the first threshold value $X_{TH-1}$, and a negative detection (indicating no detection of the target medical event) may be made if the X falls below the threshold value $X_{TH-1}$.

The medical event analyzer circuit 230 may be coupled to the data receiver circuit 210 and the user interface 220 to detect a target medical event. The medical event analyzer circuit 230 may be implemented as a part of a microprocessor circuit, which may be a dedicated processor such as a digital signal processor, application specific integrated circuit (ASIC), microprocessor, or other type of processor. Alternatively, the microprocessor circuit may be a general purpose processor that may receive and execute a set of instructions of performing the functions, methods, or techniques described herein.

The medical event analyzer circuit 230 may include circuit sets comprising one or more other circuits or sub-circuits, such as an algorithm adjuster circuit 231 and an event detector circuit 233 as illustrated in FIG. 2. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The algorithm adjuster circuit 231 may be configured to adjust the first detection algorithm to generate a different second detection algorithm 232 that is more sensitive to the target medical event than the first detection algorithm. Time, amount, or manner of adjustment of the first detection algorithm may be dependent upon patient indication, such as when the patient develops a new condition or worsening of a preexistent condition, or demonstrates an elevated risk of a particular type of disease. For example, if the patient is indicated for an AMD implant because of a high risk of syncope, then the algorithm adjuster circuit 231 may adjust the user-specified first arrhythmia detection algorithm, such that the second detection algorithm 232 is more sensitive to cardiac pause, ventricular tachyarrhythmia, or other events indicative of syncope or presyncope.

By way of example and not limitation, the algorithm adjustment may include a modification of one or more detection parameters, such as the threshold value $X_{TH}$ for the signal metric or composite metric X. In an example, the algorithm adjuster circuit 231 may adjust the first detection algorithm by reducing the first threshold value $X_{TH-1}$ to a lower second threshold value $X_{TH-2}$, that is, $X_{TH-2} < X_{TH-1}$. The resulting second detection algorithm 232, associated with the reduced threshold $X_{TH-2}$, is more sensitive to the target medical event than the first detection algorithm 231, at least because those events characterized by their corresponding signal metric or composite metric X falling between $X_{TH-2}$ and $X_{TH-1}$ (i.e., $X_{TH-2} < X < X_{TH-1}$), which may have been missed as negative detections by the first detection algorithm, may nevertheless be detected as positive detections by the second detection algorithm 232. In some examples, the algorithm adjuster circuit 231 may select the second algorithm 232 from a plurality of algorithms different from the first detection algorithm and known to be more sensitive to the target medical event according to detection performances (e.g., receiver-operating characteristic analysis) of the algorithms based on the patient historical medical events, or based on event data from a patient population.

The event detector circuit 233 may use the second detection algorithm 232 to detect a target medical event from patient physiologic signals received at the data receiver circuit 210. In an example, the target medical event includes a cardiac arrhythmia episode. The event detector circuit 233 may detect the cardiac arrhythmia using one or more of heart rates, heart rate statistics such as heart rate stability or variability, atrio-ventricular activation patterns (e.g., timing relationship between atrial activation and ventricular activation within a cardiac cycle), morphologies of cardiac electrical or mechanical signals, or hemodynamic parameters. In another example, the target medical event includes a worsened chronic medical condition, such as a worsening heart failure (WHF) event. The event detector circuit 233 may detect the WHF event using a trend of a physiologic signal metric, such as one or more of a decrease in thoracic impedance, an increase in respiration rate or a rapid-shallow breathing index (RSBI) computed as a ratio of a respiratory rate measurement to a tidal volume measurement, or an increase in intensity or timing of a heart sound component, among others. In some examples, the event detector circuit 234 may detect patient-triggered events. This may include, for example, a button push or other actuator means on the AMD 110, a handheld device, or through the user interface when the patient experiences a symptom of an onset, or a precursor, of the target physiological event.

The event detector circuit 233 may assign a detection indicator 234 to the detected medical event. The detection indicator 234 may take categorical values indicating whether or not the detected medical event, which satisfies the detection criterion of the second detention algorithm 232, would also satisfy the detection criterion of the user-specified first detection algorithm. As previously discussed, because the second detention algorithm 232 has a higher sensitivity of detection of the target medical event than the first detection algorithm, a positive detection made by the second detention algorithm 232 may not necessarily satisfy the more stringent detection criterion of the first detection algorithm. The event detector circuit 233 may distinguish the detected medical events based on whether a positive detection would have been made by the first detection algorithm. In an example, the event detector circuit 233 may assign a detection indicator 234 of "primary event" to a detected medical event that satisfies the detection criterion of the first detection algorithm, and assign a detection indicator 234 of "secondary event" to a detected medical event that does not satisfy the detection criterion of the first detection algorithm. In an example where the second detection algorithm 232 is associated with a lower detection threshold $X_{TH-2}$ than the detection threshold $X_{TH-1}$ associated with the first detection algorithm, the detected medical event may be categorized as a "primary event" if the signal metric or composite metric X meets the criterion $X>X_{TH-1}$, or categorized as a "secondary event" if X meets the criterion $X_{TH-2}<X<X_{TH-1}$.

Alternatively, the detection indicator 234 may take numerical values indicating a likelihood that the detected medical event would also satisfy the detection criterion of the first detection algorithm 231. The numerical values may be determined based on a comparison of the signal metric or composite metric X and the threshold value $X_{TH-1}$. A primary event would have also been detected by the less sensitive first detection algorithm; it thus indicates a higher likelihood of presence of an actual medical episode than a secondary event does. Among the detected primary events, the likelihood may be proportional to a difference $(X-X_{TH-1})$, such that a larger X value indicates a higher confidence of positive detection by the first detection algorithm. Among the detected secondary events, the likelihood may be inversely proportional to a difference $(X_{TH-1}-X)$, such that an event with a X value barely missing the $X_{TH-1}$ threshold has a higher likelihood of satisfying the criterion of the first detection algorithm than another event that misses the $X_{TH-1}$ threshold by a wider margin.

The event prioritizer circuit 240 may be configured to prioritize the detected medical events according to the assigned detection indicators. In an example, primary events may be assigned higher priorities than the secondary events. Among the primary events, or among the secondary events, an event with a higher numerical value of detection indicator may be assigned a higher priority than an event with a lower numerical value of the detection indicator.

In some examples, the event prioritizer circuit 240 may be configured to prioritize the detected medical event further using patient symptoms recorded during the detection of the medical event. Information of the patient symptoms may include patient description of time and/or severity of a symptom characterizing the target medical event (e.g., cardiac arrhythmia). If a detected medical event coincide in time, severity, or pattern with, or otherwise correlated to a detected medical event, then a higher priority may be assigned to a detected medical event. In some examples, patient symptoms may be indirectly represented by patient-trigged episodes, and the event prioritizer circuit 240 may be configured to prioritize detected medical events further using a comparison to a patient-triggered episode. The system 200 may register patient-triggered episodes such as when the patient demonstrates certain signs or symptoms, or experiences a precursor event indicative of a medical event (e.g., cardiac arrhythmias, syncope, or WHF events). The information about the patient-triggered episode may include patient input about presence or absence of a target medical event, severity of symptoms, timing information of the symptoms, such as onset and termination time of the patient-triggered episode, among others. The patient-triggered episode may additionally include physiological data collected in response to the patient trigger. The event prioritizer circuit 240 may correlate the physiologic data collected during a detected medical event to the physiologic data collected during a patient-triggered episode, and prioritize the detected medical events based at least on the correlation. For example, a higher priority may be assigned to a detected medical event when the correlation exceeds a threshold.

The event prioritizer circuit 240 may rank the detected events medical events, such as a plurality of arrhythmia episodes, in a specified order such as a descending order of priority. The ranked episodes, including physiologic data acquired during the detected events or optionally before or after the detected events, along with other patient data or device data, may be presented to a user or a process. In an example, the ranked episodes may be displayed on the user interface 220 for user review or adjudication. The patient physiologic data associated with the detected medical events, detection indicators, intermediate measurements or computations such as signal characteristics, episode priority information, may also be displayed. In some examples, a recommendation for adjusting AMD programming may be generated. The recommendation may include using data sensed from additional sensors to detect the target medical event. The output unit 222 may include a printer for printing hard copies of the detection information. The information may be presented in a table, a chart, a diagram, or any other types of textual, tabular, or graphical presentation formats. The presentation of the output information may include audio or other media format. In an example, the output unit 222 may generate alerts, alarms, emergency calls, or other forms of warnings to signal the user about the detected medical events.

The system 200 may include an optional therapy circuit 250 configured to deliver a therapy to the patient. In an example, the therapy may be delivered in response to the detected physiologic event satisfying a specified condition, such as being assigned a high priority. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 250 may modify an existing therapy, such as adjust a stimulation parameter or drug dosage.

Figure 3:
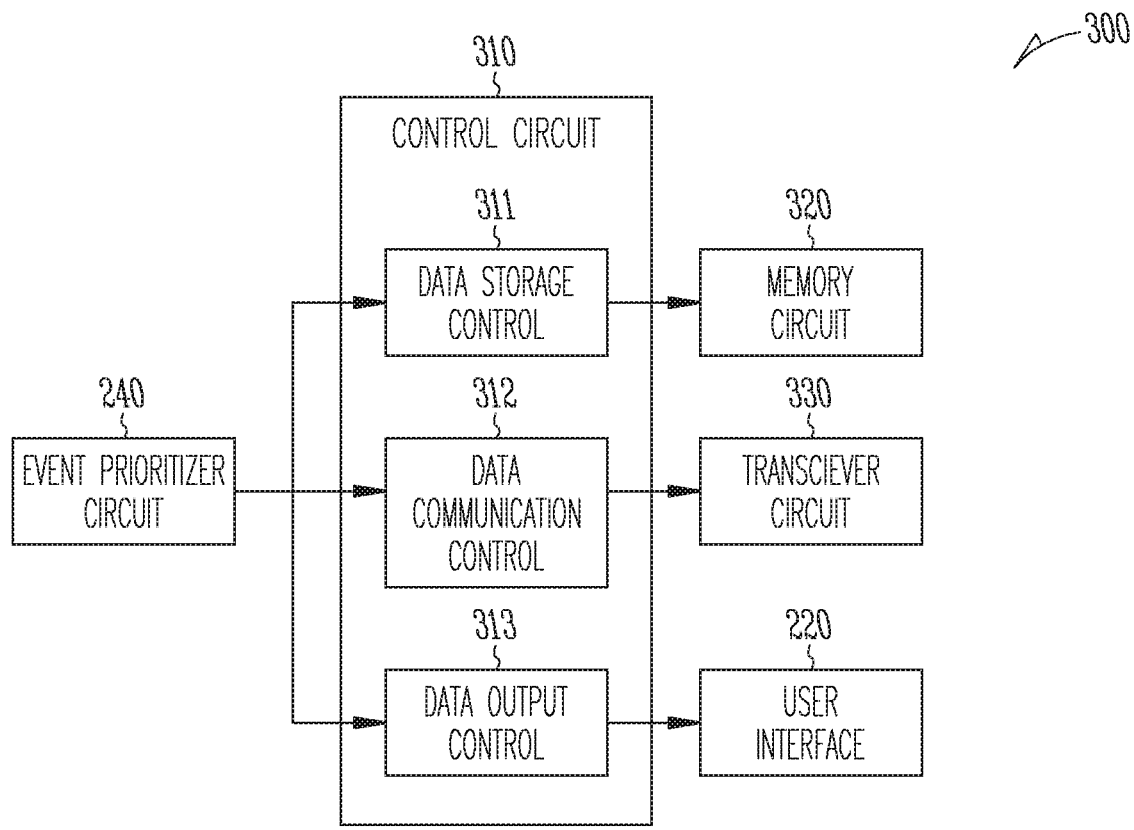
FIG. 3 illustrates portions of a priority-based medical event management system.

FIG. 3 illustrates portions of a priority-based medical event management system 300, which may be implemented in the medical event detection system 200. As previously discussed with reference to FIG. 2, the event prioritizer circuit 240 may prioritize the medical events such as detected by the event detector circuit 233 using the more sensitive second detection algorithm 232. The illustrated portions of the system 300 includes a control circuit 310 comprising one or more sub-circuits to manage the detected medical events such as arrhythmia episodes. By way of example and not limitation, the sub-circuits may include one or more of a data storage control 311, a data communication control 312, or a data output control 313 to control data storage, data transmission, or data presentation to a user or a process respectively according to prioritization of the detected medical event. The control circuit 310 may alternatively be implemented as a part of a microprocessor circuit that may receive and execute a set of instructions of performing the functions, methods, or techniques described herein. Control of medical event management (e.g., data storage, transmission, or presentation) may be executed automatically by the control circuit 310. Alternatively, at least some user intervention may be involved. For example, the prioritization of the medical events may be presented to a user such as a clinician via a user interface 220, and the control circuit 310 may receive user selection of detected medical event for data storage, transmission, or presentation.

The data storage control 311 may controllably store medical data of the detected medical events in a memory circuit 320 according to event prioritization. In an example, the order of data input/output (I/O) to the memory circuit 320 may be scheduled according to the event prioritization. Medical data of a high-priority event may be saved in the memory circuit 320 before medical data of a low-priority event. The data storage control 311 may allocate memory space according to the event priority. In an example, more memory space may be allocated for high-priority events than for low-priority events. In an example, the memory may be dynamically allocated if additional high-priority events are generated. The memory units for storing low-priority events data may be re-allocated for high-priority events. The stored low-priority event data may be overwritten by high-priority event data.

Generally, a primary event has a higher priority than a secondary event. The data storage control 311 may prioritize storage of medical data associated with a primary event over storage of medical data associated with a secondary event. For events within the same category of primary events or of secondary events, storage of medical data associated with an event having a higher likelihood of satisfying the detection criterion of the first detection algorithm may be prioritized over storage of medical data associated with an event having a lower likelihood of satisfying the detection criterion of the first detection algorithm.

The data communication control 312 may control data communication such as transmission of the medical data of the detected medical events to an external system. In an example, the system 300 may include an AMD, such as the AMD 110 in FIG. 1. The AMD comprises one or more of the data receiver circuit 210, the medical event circuit 230, and the control circuit 310. The AMD may be operatively in communication with an external system, such as the external system 125 in FIG. 1. The AMD may include a transceiver circuit 330 configured to perform data communication with the external system, including transmitting to the external system the medical data associated with the detected medical events. The transceiver circuit 330 may also receive programming instructions from the external system. The data communication control 312 may control the transmission of the medical data to the external device according to the event prioritization. In an example, the data communication control 312 may allocate communication bandwidth according to the event prioritization. For example, more bandwidth may be allocated for transmitting the medical data associated with high-priority events than for medical data associated with low-priority events. In another example, medical data associated with high-priority events may be transmitted prior to the medical data associated with low-priority events. The event priority-based control of communication timing, sequence, or bandwidth may help clinicians timely attend to medical events with higher clinical significance or of higher clinical interest, such that expert review or clinical intervention may be provided as needed.

In an example, the data communication control 312 may prioritize transmission of medical data associated with a primary event over transmission of medical data associated with a secondary event. For events within the same category of primary events, or the same category of secondary events, transmission of medical data associated with an event having a higher likelihood of satisfying the detection criterion of the first detection algorithm may be prioritized over transmission of medical data associated with an event having a lower likelihood of satisfying the detection criterion of the first detection algorithm.

The data output control 313 may control data output such as presentation of medical data associated with the detected medical events to a user via the user interface 220. In an example, the order of medical event presentation may be scheduled according to the event priority. Medical data associated with a high-priority event may be presented to the user before medical data associated with low-priority event. In an example, the data output control 313 may prioritize data presentation of a primary event over data presentation of a secondary event. For events within the same category of primary events, or the same category of secondary events, presentation of medical data associated with an event having a higher likelihood of satisfying the detection criterion of the first detection algorithm may be prioritized over presentation of medical data associated with an event having a lower likelihood of satisfying the detection criterion of the first detection algorithm. Examples of priority-based presentation of medical data associated with detected medical events according to event priority are discussed below, such as with reference to FIG. 4.

In some examples, medical data associated with detected medical events may be post-processed before being presented to the user interface 220, stored in the memory circuit 320, or transmitted to an external system via the transceiver circuit 330. One example of the post-processing includes a data reduction operation, which is used to improve efficient usage of device resources such as device memory, transmission bandwidth, power consumption, and computational resources. Data reduction may be carried out according to the event priority. In an example, data reduction operation may include down-sampling operation or digitization of the data samples. In an example, medical data associated with a low-priority event may be post-processed with a higher data reduction rate than a higher priority event, such that the low-priority event has a lower sampling rate and/or a lower resolution than a high-priority event. In another example, data reduction operation may include data truncation, such that a selected portion of the medical data is used for data presentation, storage, or transmission. The truncated medical data associated with low-priority events may have a shorter duration or data volume than the truncated medical data associated with high-priority events.

Figure 4:
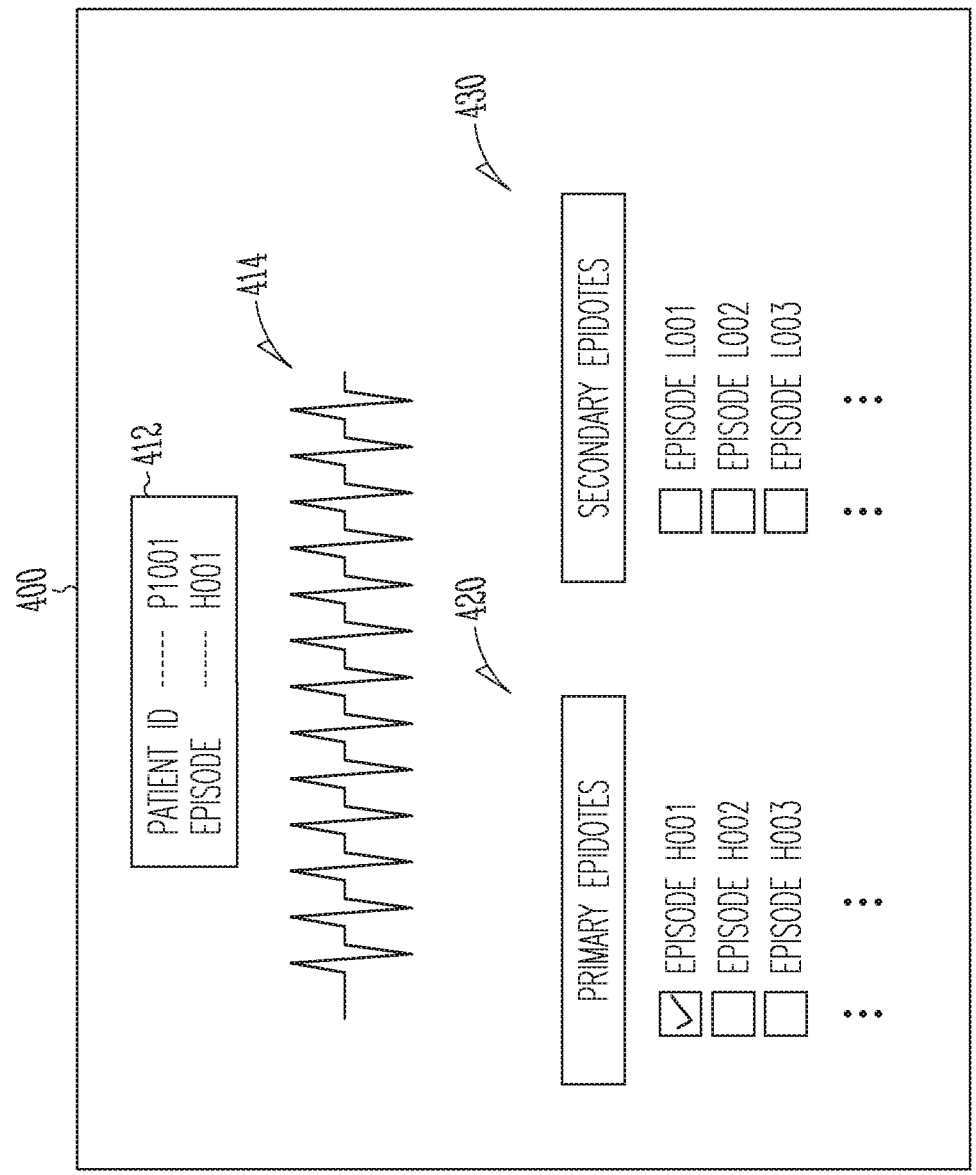
FIG. 4 illustrates an example of at least a portion of a user interface for interactive display of medical data associated with a detected medical event.

FIG. 4 illustrates an example of at least a portion of a user interface 400 for interactive display of medical data associated with a detected medical event and receiving user command or annotation. The user interface portion 400, which is an embodiment of the display unit of the user interface 220, includes a display of an episode of a medical event detected by a medical device, such as the AMD 110. The displayed information may include patient identification (e.g., P1001) and episode identifier (e.g., H001) 412 and recorded physiologic data 414 associated with the selected episode (which is H001 in this example). The physiologic data 414 may be sensed using electrodes or physiologic sensors in communication with the medical device, and collected during, or alternatively before or after, the detected medical event. By way of example and as illustrated in FIG. 4, the physiologic data 414 includes an electrogram sensed at a cardiac site, such as a ventricle or an atrium. In some examples, two or more physiologic signals may be displayed, such as EGMs from multiple cardiac sites or via different sensing electrode configurations, cardiac mechanical signals, or hemodynamic signals sensed from one or more sensors. In some examples, a marker channel including information about within-channel or inter-channel timing and the type of detected events (such as sensed or paced heart beats) may also be displayed.

The user interface 400 may include a summary of the medical events detected from the patient using the more sensitive second detection algorithm than the user-specified first detection algorithm. The summary may include detection indicators for the detected events each indicating a likelihood that the detected arrhythmia episode satisfies the detection criterion of the first detection algorithm. By way of example and as illustrated in FIG. 4, the summary includes identifiers of a list of primary episodes 420 and identifiers of a list of secondary episodes 430. The primary episodes are arrhythmia episodes that also satisfy the more stringent detection criterion of the users-specified first detection algorithm. The secondary episodes are arrhythmia episodes that do not satisfy the detection criterion of the users-specified first detection algorithm. A user may select a primary episode or a secondary episode to be displayed on the user interface, and interactively adjudicate the displayed episode such as to provide annotation of arrhythmia type. The selection may be achieved using check boxes (as shown), radio buttons, drop down lists, list boxes, buttons, toggles, text fields, among other input control elements on the user interface 400. FIG. 4 illustrates displaying the stored EGM data 414 for a selected primary episode H001. In an example, episodes within the same category (e.g., the primary episodes, or the secondary episodes) may be ranked in an order such as a descending order of the priority, as discussed above with reference to the event prioritizer circuit 240. In some examples, a graphical or textual indicator (e.g., a blinking icon) may be displayed on the user interface, alerting the user that one or more secondary arrhythmia events have been detected using the more sensitive second detection algorithm, and that the corresponding episode data are available for review. In response to a user command, more details of the secondary episodes such as ranked list of episodes shown in FIG. 4 may be displayed. A user may be prompted to select from the ranked list a secondary episode to review. In an example, if an AMD does not detect an arrhythmia under a user-specified first detection algorithm, but the patient complains about symptoms of arrhythmia, a clinician may choose to retrieve and review secondary episodes to ascertain proper device programming.

Detection and storage of episodes of secondary events corresponding to a less stringent criterion (a higher sensitivity), as discussed in this document, may allow the device to detect additional arrhythmia events that would otherwise be missed by the less sensitive user-specified algorithm. Using a user interface such as the one shown in FIG. 4, a user may interactively inspect and adjudicate the secondary episodes, and adjust device programming to achieve improved arrhythmia detection performance in an AMD. For example, based on the adjudication of the secondary episodes, a user may determine an individualized sensitivity level (e.g., detection threshold) for arrhythmia detection, which may reduce FN detections and improve arrhythmia detection sensitivity, thereby improving the functionality of the AMD.

Figure 5:
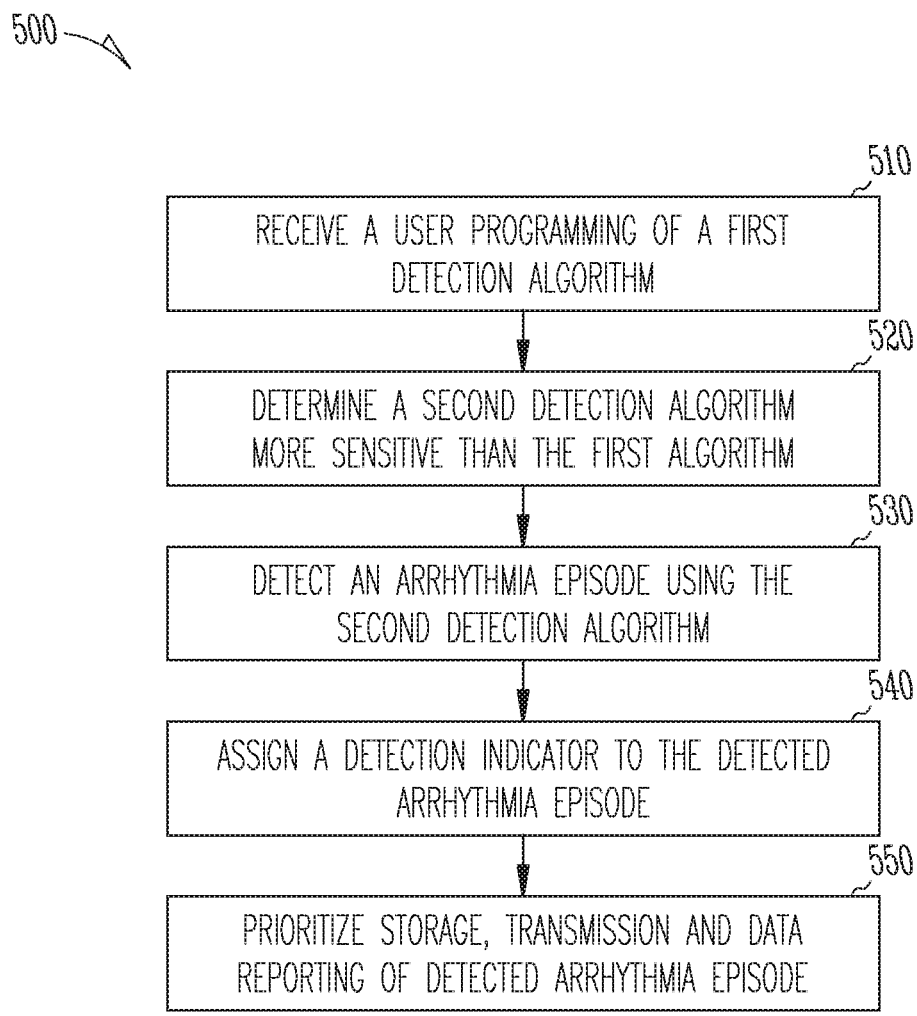
FIG. 5 illustrates generally an example of a method for monitoring cardiac arrhythmias.

FIG. 5 illustrates generally an example of a method 500 for monitoring cardiac arrhythmias, such as atrial fibrillation, atrial flutter, atrial tachycardia, supraventricular tachycardia, ventricular tachycardia, or ventricular fibrillation, among other atrial or ventricular brady- or tachy-arrhythmia. The method 500 may be implemented and executed in an ambulatory medical device, such as an implantable or wearable medical device, or in a remote patient management system. In an example, the method 500 may be implemented in, and executed by, the AMD 110, one or more devices in the external system 125, or the medical event detection system 200.

The method 500 commences at 510, where a user programming of a first detection algorithm for detecting a target medical event (e.g., a type of cardiac arrhythmia) may be received, such as via the user interface 220. The first detection algorithm may include a detection criterion that a signal metric or a composite signal metric, generated from one or more physiologic signals, must satisfy so as to make a positive detection decision of the target medical event. In an example of arrhythmia detection, the detection criterion of the first algorithm may include a threshold value ($X_{TH-1}$) for the corresponding signal metric or composite metric X. A positive detection of a specified type of arrhythmia (e.g., atrial fibrillation) may be made if $X>X_{TH-1}$; and a negative detection indicating an absence of the arrhythmia type may be made if $X<X_{TH-1}$.

At 520, a second detection algorithm, different from and has a higher sensitivity in detecting the cardiac arrhythmia than the received first detection algorithm, may be generated, such as by using the algorithm adjuster circuit 231. The second detection algorithm may be selected from a plurality of candidate algorithms that are known to be more sensitive than the received first detection algorithm, based on the patient historical medical events or based on event data from patient population. Alternatively, the second detection algorithm may be generated by adjusting a parameter of the first detection algorithm. Time, amount, or manner of adjustment of the first detection algorithm may be dependent upon patient indication, such as when the patient develops a new condition or worsening of a preexistent condition, or demonstrates an elevated risk of a particular type of disease. In an example, the second detection algorithm differs from the first detection algorithm by at least the detection threshold value $X_{TH}$ associated with the signal metric or composite metric X. The second detection algorithm may be generated by reducing the threshold ($X_{TH-1}$) of the first detection algorithm to a lower threshold ($X_{TH-2}$). With a lower detection threshold $X_{TH-2}$, those events associated with the signal metric or composite metric X that fall between $X_{TH-2}$ and $X_{TH-1}$ may more likely be detected as arrhythmic events.

At 530, the second detection algorithm may be used to detect the target medical event (e.g., arrhythmia detection) from patient physiologic signals, such as via the event detector circuit 233. The physiologic signals may be sensed using one or more implantable, wearable, or otherwise ambulatory sensors or electrodes associated with the patient. The sensors may be incorporated into, or otherwise associated with an ambulatory device such as the AMD 110. Alternatively, the patient physiologic signals may be stored in a storage device, such as an electronic medical record (EMR) system, and may be retrieved for analysis in response to a user command. In an example, cardiac arrhythmia may be detected using one or more of heart rates, heart rate statistics such as heart rate stability or variability, atrioventricular activation patterns (e.g., timing relationship between atrial activation and ventricular activation within a cardiac cycle), morphologies of cardiac electrical or mechanical signals, or hemodynamic parameters. In another example, worsening heart failure (WHF) event may be detected using a trend of a physiologic signal metric, such as one or more of a decrease in thoracic impedance, an increase in respiration rate or a rapid-shallow breathing index (RSBI) computed as a ratio of a respiratory rate measurement to a tidal volume measurement, or an increase in intensity or timing of a heart sound component, among others.

At 540, a detection indicator may be assigned to the detected arrhythmia episode. The detection indicator may take categorical values indicating whether or not the detected medical event, which satisfies the detection criterion of the second detention algorithm, would also satisfy the detection criterion of the first detection algorithm. In an example, a "primary event" indicator may be assigned to a detected medical event that also satisfies the detection criterion of the first detection algorithm, and a "secondary event" indicator may be assigned to a detected medical event that does not satisfy the detection criterion of the first detection algorithm. The "primary events" may include the detected medical events with the signal metric or composite metric X satisfying the criterion $X>X_{TH-1}$. The "secondary events" may include the detected medical events satisfying the condition $X_{TH-2}<X<X_{TH-1}$.

The detection indicator may alternatively take numerical values indicating a likelihood that the detected medical event would also satisfy the detection criterion of the first detection algorithm. The numerical values may be determined based on a comparison of the signal metric or composite metric X and the threshold value $X_{TH-1}$. Primary events would have also been detected by the less sensitive first detection algorithm, therefore may have a higher likelihood of an occurrence of an actual medical episode than the secondary events. Among the detected primary events, the likelihood may be proportional to a difference $(X-X_{TH-1})$, such that a larger X value indicates higher confidence of the positive detection by the first detection algorithm. Among the detected secondary events, the likelihood may be inversely proportional to a difference $(X_{TH-1}-X)$, such that an event with a X value barely miss the $X_{TH-1}$ threshold has a higher likelihood of satisfying the criterion of the first detection algorithm than another event that miss the $X_{TH-1}$ threshold by a wider margin.

At 550, the detected medical events may be prioritized according to the assigned detection indicators. In an example, primary events may have higher priorities than the secondary events. Among the primary events, or among the secondary events, an event with a higher numerical value of detection indicator may have a higher priority than an event with a lower numerical value of the detection indicator. The prioritization of the detected medical event may further be based on patient symptom recorded during the detection of the medical event. Patient symptom may include patient description of time and/or severity of a symptom characterizing the target medical event. Alternatively or additionally, the symptoms may be indirectly represented by patient-trigged episodes. The detected medical events may be prioritized using a correlation between the physiologic data collected during a detected medical event and the physiologic data collected during a patient-triggered episode. A higher priority may be assigned to a detected medical event when the correlation exceeds a threshold.

The detected events medical events, such as a plurality of arrhythmia episodes, may be ranked in a specified order of the priority (e.g., a descending order of priority) for episode data storage, transmission, and reporting, such as by using the control circuit 310. In an example, medical data associated with a high-priority event (e.g., a primary event) may be stored in storage device before medical data associated with low-priority event (e.g., a secondary event), and/or more memory space may be allocated for a high-priority event (e.g., a primary event) than for a low-priority event (e.g., a secondary event). For events within the same category (e.g., primary events, or secondary events), an event with a higher likelihood of satisfying the detection criterion of the first detection algorithm may have a higher priority of being stored in the storage device than an event having a lower likelihood of satisfying the detection criterion of the first detection algorithm.

In another example, medical data associated with medical events, such as sensed and acquired by the AMD 110, may be transmitted to an external system based on the event prioritization. For example, medical data associated with a primary event may be transmitted prior to the transmission of medical data associated with a secondary event. Additionally or alternatively, more bandwidth may be allocated for transmitting data associated with the primary events than for data associated with secondary events. For events within the same category (e.g., primary events, or secondary events), transmission of medical data associated with an event having a higher likelihood of satisfying the detection criterion of the first detection algorithm may be prioritized over transmission of medical data associated with an event having a lower likelihood of satisfying the detection criterion of the first detection algorithm.

In yet another example, the detected medical events may be presented to a user in an order of event priority. Medical data associated with a high-priority event (e.g., a primary event) may be presented to the user before medical data associated with low-priority event (e.g., a secondary event). For events within the same category (e.g., primary events, or secondary events), presentation of medical data associated with an event having a higher likelihood of satisfying the detection criterion of the first detection algorithm may be prioritized over presentation of medical data associated with an event having a lower likelihood of satisfying the detection criterion of the first detection algorithm. In an example, a graphical or textual indicator may be displayed on the user interface to alert the detection of one or more secondary arrhythmia events at more sensitive settings and that the corresponding episodes stored in the device are available for review, as illustrated in FIG. 4. In response to a user command, more details of the secondary episodes such as ranked list of episodes may be displayed. A user is prompted to select a secondary episode to review. For example, if an AMD does not detect arrhythmia under a user-specified device setting, but the patient complains about symptoms indicative of event episodes, a clinician may choose to retrieve and review secondary episodes to ascertain proper device programming.

Figure 6:
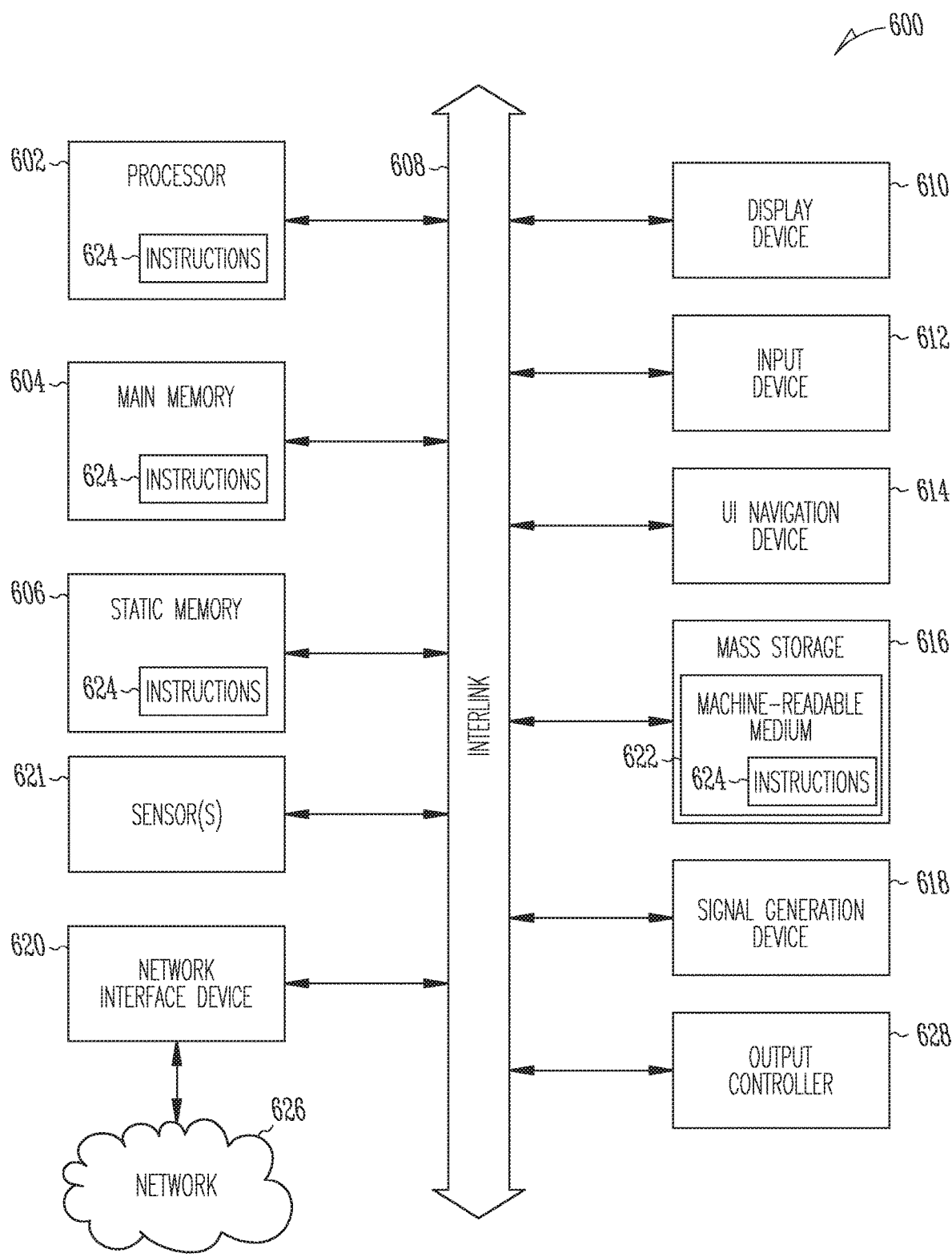
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communication network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communication network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for monitoring cardiac arrhythmia, comprising:
  an arrhythmia detector circuit configured to:
    receive a physiologic signal and a first detection algorithm having a first sensitivity, the first detection algorithm including a detection criterion for detecting a cardiac arrhythmia;
    detect an arrhythmia episode from the physiologic signal using a second detection algorithm having a second sensitivity higher than the first sensitivity than the first detection algorithm to prevent or reduce false negative detection of the cardiac arrhythmia; and
    determine a detection indicator for the arrhythmia episode detected by the second detection algorithm, the detection indicator indicating a likelihood that the detected arrhythmia episode satisfies the detection criterion of the first detection algorithm;
  an event prioritizer circuit configured to prioritize the detected arrhythmia episode according to the detection indicator; and
  a user interface configured to:
    display the detected arrhythmia episode if the detection indicator indicates that the detected arrhythmia episode satisfies the detection criterion of the first detection algorithm; and
    provide an indication to a user that the detected arrhythmia episode is stored and displayable on demand if the detection indicator indicates that the detected arrhythmia episode does not satisfy the detection criterion of the first detection algorithm.

2. The system of claim 1, wherein the arrhythmia detector circuit is configured to generate the second detection algorithm by adjusting one or more detection parameters of the first detection algorithm.

3. The system of claim 2, wherein the one or more detection parameters include a first detection threshold, and the arrhythmia detector circuit is configured to generate the second detection algorithm by reducing the first detection threshold to a lower second detection threshold.

4. The system of claim 1, comprising a memory circuit configured to store the detected arrhythmia episode, and a control circuit is configured to prioritize storage of the detected arrhythmia episode in the memory circuit according to the prioritization of the arrhythmia episode.

5. The system of claim 4, wherein the control circuit is configured to prioritize storage of a detected arrhythmia episode that satisfies the detection criterion of the first detection algorithm over storage of another detected arrhythmia episode that does not satisfy the detection criterion of the first detection algorithm.

6. The system of claim 1, comprising an ambulatory device communicatively coupled to an external device, the ambulatory device including a transceiver circuit and one or more of the arrhythmia detector circuit and the event prioritizer circuit, wherein the transceiver circuit is configured to transmit the detected arrhythmia episode to the external device according to the prioritization of the arrhythmia episode.

7. The system of claim 6, comprising a control circuit configured to prioritize transmission of a detected arrhythmia episode that satisfies the detection criterion of the first detection algorithm over transmission of another detected arrhythmia episode that does not satisfy the detection criterion of the first detection algorithm.

8. The system of claim 1, comprising an output circuit configured to present the detected arrhythmia episode to a user or a process, and a control circuit configured to prioritize presentation of the detected arrhythmia episode according to the prioritization of the arrhythmia episode.

9. The system of claim 8, wherein the control circuit is configured to prioritize a presentation of a detected arrhythmia episode that satisfies the detection criterion of the first detection algorithm over a presentation of another arrhythmia episode that does not satisfy the detection criterion of the first detection algorithm.

10. The system of claim 1, wherein the event prioritizer circuit is configured to prioritize the detected arrhythmia episode further using a comparison to a patient-triggered episode.

11. The system of claim 1, wherein the event prioritizer circuit is configured to prioritize the detected arrhythmia episode further using a comparison to patient symptom.

12. The system of claim 1, comprising a therapy circuit configured to generate a therapy for treating arrhythmia in response to the detection of the arrhythmia episode.

13. A method for monitoring cardiac arrhythmias using a cardiac monitoring system, the method comprising:
  receiving a user programming of a first detection algorithm having a first sensitivity, the first detection algorithm including a detection criterion for detecting a cardiac arrhythmia;
  determining a second detection algorithm based on the received first detection algorithm via an arrhythmia detector circuit, the second detection algorithm having a second sensitivity higher than the first sensitivity than the first detection algorithm to prevent or reduce false negative detection of the cardiac arrhythmia;
  detecting an arrhythmia episode from a physiologic signal via the arrhythmia detector circuit using the second detection algorithm;
  determining a detection indicator for the arrhythmia episode detected by the second detection algorithm via the arrhythmia detector circuit, the detection indicator indicating a likelihood that the detected arrhythmia episode satisfies the detection criterion of the first detection algorithm;
  prioritizing the detected arrhythmia episode via an event prioritizer circuit according to the detection indicator;
  displaying the detected arrhythmia episode if the detection indicator indicates the detected arrhythmia episode satisfies the detection criterion of the first detection algorithm; and
  providing an indication to a user that the detected arrhythmia episode is stored and displayable on demand if the detection indicator indicates the detected arrhythmia episode does not satisfy the detection criterion of the first detection algorithm.

14. The method of claim 13, wherein determining the second detection algorithm includes adjusting one or more detection parameters of the first detection algorithm.

15. The method of claim 14, wherein adjusting the one or more detection parameters includes reducing a first detection threshold of the first detection algorithm to a lower second detection threshold of the second detection algorithm.

16. The method of claim 13, comprising storing the detected arrhythmia episode in a memory circuit according to the prioritization of the arrhythmia episode.

17. The method of claim 13, comprising transmitting the detected arrhythmia episode to an external device according to the prioritization of the arrhythmia episode.

18. A system for monitoring cardiac arrhythmia, comprising:
an arrhythmia detector circuit configured to:
receive a physiologic signal;
determine a presence of an arrhythmia in the physiologic signal using a first detection algorithm having a first sensitivity; and
for the same physiologic signal, determine the presence of the arrhythmia in the physiologic signal using a second detection algorithm having a second sensitivity higher than the first sensitivity than the first detection algorithm to prevent or reduce false negative detection by the first detection algorithm; and
a user interface configured to:
display the physiologic signal in response to the presence of the arrhythmia determined by the first detection algorithm and the presence of the arrhythmia determined by the second detection algorithm; and
provide an indication to a user that the physiologic signal is stored and displayable on demand in response to the presence of the arrhythmia determined by the second detection algorithm and no presence of the arrhythmia determined by the first detection algorithm.

19. The system of claim 18, wherein the first detection algorithm includes a first detection threshold, and the second detection algorithm includes a second detection threshold lower than the first detection threshold.

20. The system of claim 18, comprising a control circuit configured to prioritize storage of the physiologic signal in a memory device, or to prioritize transmission of the physiologic signal to an external device, based on at least one of the presence of the arrhythmia determined by the first detection algorithm or the presence of the arrhythmia determined by the second detection algorithm.

* * * * *